United States Patent [19]

Parker et al.

[11] Patent Number: 5,118,819
[45] Date of Patent: Jun. 2, 1992

[54] PROCESS FOR THE PREPARATION OF DELTA-3-CARENE DIADDUCTS

[75] Inventors: David W. Parker; Walter C. Frank, both of Holland, Pa.

[73] Assignee: Union Camp Corporation, Wayne, N.J.

[21] Appl. No.: 680,171

[22] Filed: Apr. 3, 1991

[51] Int. Cl.$^5$ .......................................... C07D 307/94
[52] U.S. Cl. ................................... 549/237; 549/233; 528/403
[58] Field of Search ................... 528/87, 403; 549/233, 549/236, 237

[56] References Cited

U.S. PATENT DOCUMENTS

| | | | |
|---|---|---|---|
| 4,107,420 | 8/1978 | Schluenz et al. | 526/237 |
| 4,946,969 | 8/1990 | Parker | 549/237 |
| 5,041,561 | 8/1991 | Parker | 549/237 |

Primary Examiner—John Kight, III
Assistant Examiner—Richard Jones
Attorney, Agent, or Firm—William K. Wissing

[57] ABSTRACT

A process for the preparation of a carene-dienophile diadduct in high yield is provided. Delta-3-carene is reacted with a Diels-Adler dienophile, preferably maleic anhydride, at a dienophile:carene molar ratio of at least 1.5:1 and a temperature of at least 150° C. The diadduct produced by the reaction of delta-3-carene and a Diels Alder dienophile, preferably maleic anhydride, is useful as a curing agent in epoxy resin systems.

19 Claims, No Drawings

PROCESS FOR THE PREPARATION OF DELTA-3-CARENE DIADDUCTS

BACKGROUND OF THE INVENTION

This invention relates to the preparation of diadduct products formed from the reaction of a Diels-Alder dienophile and delta-3-carene, and more specifically, to the high yield preparation of maleic anhydride diadducts of delta-3-carene. The invention also relates to the use of the diadducts as curing agents for epoxy resin systems. The cured resins are useful in the manufacture of electronic components.

The class of compounds known as terpenes are usually defined as a variety of unsaturated $C_{10}H_{16}$ compounds, either cyclic or acyclic, which are based on the isoprene unit. A conjugated terpene contains two carbon-carbon double bonds, separated by a single bond. Delta-3-carene is an unconjugated, monounsaturated, bicyclic terpene. It is well known that Diels-Alder dienophile monoadducts of terpenes, which are herein defined as molecules that result upon reaction of one molecule of a Diels-Alder dienophile and one molecule of a terpene, can be prepared simply by contacting the reactants at elevated temperatures. Minor amounts of diadducts, which are herein defined as molecules that result upon reaction of two molecules of a Diels-Alder dienophile and one molecule of a terpene, can also form upon contact at elevated temperatures. Not all terpenes can react to form a diadduct product however, for example, alpha-terpinene only forms a monoadduct product, and therefore, accurate predictions as to whether a terpene will produce a diadduct product cannot be made.

Although the reaction of terpenes with maleic anhydride, a typical Diels-Alder dienophile, has been reported, for example in U.S. Pat. No. 1,993,031 issued to Peterson, the particular use of delta-3-carene to produce a diadduct has not been reported.

Prior experimentation with delta-3-carene and maleic anhydride was conducted by Sugathan and Verghese and reported in "Studies in Terpenes. Part XI. A Contribution to the Understanding of the Diels-Alder Reaction of 3-Carene with Maleic Anhydride", K. K. Sugathan and J. Verghese, *Journal Indian Chem. Soc.. Vol.* 40. No. 2 (1963). Sugathan and Verghese reported an experiment in which maleic anhydride was reacted with delta-3-carene in a 2:1 molar ratio in the presence of acetone, leading to a residue product which contained an adduct product, but no diadduct product was reported. They also reported an experiment using a 1:1 molar ratio at 165°-265° C., in a solventless reaction, again with no diadduct reportedly formed. The article reports that delta-3-carene, when reacted with maleic anhydride, furnishes only a mixture of monoadduct products. The article illustrates the perception in the art that delta-3-carene exhibits only minor reactivity with maleic anhydride, and that delta-3-carene would not react with maleic anhydride to produce diadduct product.

U.S. Pat. No. 4,019,921 to Koebner discloses a condensation product of the reaction of the unsaponifiable constituents of tall oil and maleic anhydride. The tall oil is described as having a low boiling range (60°-145° C.) cut containing the compound carene along with other known constituents identified as alpha- and beta- pinenes, camphene, and terpineol. This low boiling cut accounted for 13% of the entire tall oil mixture. Koebner did not report whether any diadducts were produced in his reaction process.

The prior art has studied the reactions between other terpenes and maleic anhydride to increase the yield of diadduct products, but there is scarce coverage of the reactions involving delta-3-carene. Higher yields of the diadduct products are desirable since the process of separating a diadduct from its corresponding monoadduct is expensive and time-consuming.

U.S. Pat. No. 4,107,420, to Schluenz et al, discloses a process for reacting non-conjugated monocyclic terpenes and maleic anhydride in equimolar amounts, preferably at temperatures between 140° C. and 200° C., in the presence of iodine. Schluenz et al claim that a diadduct product in yields of greater than 15% can be achieved, and the examples disclose a product of 45% diadduct being formed. However, the reference does not identify delta-3-carene as a possible terpene compound for use in the Schluenz et al process.

It is an object of this invention to provide diadducts of delta-3-carene and various Diels-Alder dienophiles.

It is a further object of this invention to provide diadducts of delta-3-carene and a Diels-Alder dienophile in relatively high yield relative to the formation of monoadducts.

It is yet a further object of this invention to provide a cured epoxy resin, which is the curing-reaction product of an epoxy compound and diadducts of delta-3-carene and an anhydride which is reactive in a Diels-Alder dienophile manner, having a high glass transition temperature.

SUMMARY OF THE INVENTION

The present invention provides a process for the high yield production of diadducts of delta-3-carene and a dienophile, wherein production of the diadduct is favored over production of the monoadduct. The process comprises heating a mixture of Diels-Alder dienophile and delta-3-carene at a temperature of at least about 150° C. and a molar ratio of at least about 1.5:1 until the reaction product is greater than about 50% by weight diadduct.

The process is preferably conducted at a temperature of at least about 165° C., and more preferably between about 175°-200° C. In a more preferred embodiment, the reaction is conducted at a molar ratio of dienophile to delta-3-carene of at least about 2:1. The preferred Diels-Alder dienophile is maleic anhydride. It has been found that a major proportion of the product of the reaction of this invention is the diadduct and that the product is substantially free of monoadduct. That is, at least about 70% of the adduct product is diadduct. Generally, about 70%-90% by weight of adduct product is the diadduct.

The Diels-Alder dienophile diadducts of delta-3-carene are expected to find extensive commercial use. The unique dianhydride adducts of delta-3-carene can be used as coating agents and as ink components. Also, these unique diadducts can be useful as epoxy curing agents. Upon reaction with an epoxy compound, these agents provide cured epoxy resin, to be used in, for example, films, coatings and articles characterized by a high glass transition temperature. Such resins are useful in the printed circuit board industry and for other electronic uses.

DESCRIPTION OF THE PREFERRED EMBODIMENT

According to the present invention, a process for producing a diadduct product of delta-3-carene and a Diels-Alder dienophile in high yield is provided which comprises reacting the Diels-Alder dienophile and delta-3-carene, in a molar ratio of at least 1.5:1 and at a temperature of at least 150° C., for a time sufficient to provide a reaction product which is greater than about 50% by weight diadduct. The present invention further provides a cured epoxy product having a high glass transition temperature which is prepared by reacting the delta-3-carene diadduct with an epoxy compound.

The reaction process of this invention is conducted at a temperature of at least about 150° C., preferably at least about 165° C., and more preferably at a Range of about 175°-200° C. The quantitative ratios of the reactants for the diadduct process can vary. The molar ratio of Diels-Alder dienophile to delta-3-carene is at least 1.5:1, preferably in the range of 2-3:1, with a most preferred range of about 2-2.5:1.

The delta-3-carene reactant is commercially available from various sources. The reaction can be performed utilizing either technical grade delta-3-carene or with high purity grade delta-3-carene (98% wt. delta-3-carene or greater). The high purity grade product is preferred.

The reaction is preferably conducted in the absence of a solvent, instead using the reactants in molten state to provide the liquid medium of the reaction. The Diels-Alder dienophiles that can be used in the reaction are preferably those whose normal boiling points exceed the reaction temperature, permitting the reaction to be conducted at atmospheric pressure. Suitable dienophiles includes maleic anhydride, which is preferred, itaconic anhydride, maleimides, and fumarates. The reaction can be conducted simply by heating a mixture of the dienophiles and delta-3-carene to the reaction temperature, but the reaction is preferably conducted by first melting and heating the dienophile to the reaction temperature and then adding the delta-3-carene to the molten dienophile. Lower-boiling dienophiles such as acrylonitrile, acrylic acid, methacrylic acid, and lower alkyl esters of these, such as methyl acrylate, can also be used if the reaction is conducted under pressure to ensure a liquid-state at the desired temperature. As will be appreciated by one of skill in the art, virtually any of the known Diels-Alder dienophiles can be advantageously employed by manipulating the reaction pressure to ensure a liquid-state reaction temperature of at least 150° C.

Although the reaction is preferably conducted without solvent, a solvent can nevertheless be employed. Suitable solvents, are aromatic hydrocarbons, esters, diesters, ethers, and polyethers. Representative solvents are p-cymene and 2-methoxyethyl ether.

In a preferred embodiment, the diadduct process is conducted at about 175°-200° C. at atmospheric pressure, and in the absence of solvent. The maleic anhydride and delta-3-carene are combined in a molar ratio of about 2:1, and this mixture is heated to the reaction temperature. Alternatively, one reactant can be heated, in molten state, to the reaction temperature, after which the other reactant is added to it. Most preferred is to melt the maleic anhydride, heat it in molten state to the reaction temperature, and then add the delta-3-carene.

In all processes according to the invention, the reaction is allowed to proceed until the reaction product formed is greater than about 50% by weight of the diadduct product based upon reacting only the delta-3-carene and the dienophile on a 100% purity basis. That is, the reaction proceeds until the weight of diadduct produced is greater than 50% of the combined weight of dienophile and delta-3-carene charged initially as reactants (on a 100% purity basis), i.e., the yield of the diadduct is greater than 50%. Most preferably, the reaction is allowed to proceed until the yield of diadduct product is from about 70% to 90%. This reaction may also be allowed to proceed until the reaction is complete, that is, until no further adduction is possible. The reaction product can be characterized as a delta-3-carene diadduct formed substantially free of monoadduct. The reaction products are then separated by distillation to isolate the adduct products from any unreacted materials and any reaction by-products. This distillation can be carried out under vacuum conditions. The adduct product is rich in diadduct, the weight ratio of diadduct to monoadduct generally being about 70:30 to 90:10. The monoadduct product is separated from the diadduct product by further distillation wherein the monoadduct is the distillate and the diadduct product is the retained residue. The preferred distillation process is vacuum distillation. The final diadduct product is at least 90% by weight diadduct and as pure as 99% by weight diadduct or greater.

The diadduct product of delta-3-carene and an anhydride, such as maleic or itaconic anhydride, is useful as a curing agent in epoxy resin systems. Epoxy resins cured with such a diadduct exhibit a high glass transition temperature. The epoxy resin is formed by combining the diadduct product with an epoxy compound to effect cure of the epoxide according to standard conditions for epoxy system cure.

In a preferred curing reaction, the diadduct product of the present invention formed by the reaction of maleic anhydride and delta-3-carene is added to an epoxy compound that has been pre-heated to about 100° C. It is preferred that the diadduct be of at least 90% weight purity, and most preferably at least about 95% by weight diadduct. Examples of epoxy compounds that are beneficially cured with the diadduct of the invention are Epon resins, preferably Epon 828 manufactured by Shell Chemical Co. of Houston, Tex., ERL resins, preferably ERL 4221 manufactured by Union Carbide of Danbury, Conn., and D.E.R. resins, including those selected from the 300, 400, 500, 600, or 700 series manufactured by Dow Chemical Co. of Midland, Mich. The preferred epoxy compounds are the condensation products of epichlorohydrin with a bisphenol, such as bisphenol-A. The most preferred epoxy resin is Epon 828. After the diadduct is added to the epoxide, the mixture is heated to a curing temperature, generally in the range of about 200°-280° C. Preferably the curing temperature is about 220°-250° C. The mixture is permitted to cure for about 2-24 hours. The epoxy resins so produced are characterized by a high glass transition temperature, generally at least about 200° C. Such resins are useful as coatings and in the electronics industry as dielectric components.

EXAMPLE 1

A 250 ml flask was charged With 147.1 g (1.5 mol) maleic anhydride and 102.2 g (0.74 mol) of 98% pure delta-3-carene. This mixture was heated under an inert atmosphere to 175° C., and maintained at that temperature for 29.5 hours. Unreacted maleic anhydride and terpenes were then removed by vacuum distillation to yield 222.4 grams of a mixture comprising about 75% diadduct and about 25% monoadduct. The saponification number of the mixture was 633, and the Mettler dropping point was 100.7° C.

EXAMPLE 2

A 250 ml flask was charged with 102 g (0.74 mol) of 98% pure delta-3-carene, and this was heated to 170° C. under an inert atmosphere. During the course of 3.5 hours, 147 g (1.5 mol) of maleic anhydride were added to the flask. The reactants were maintained at 180° C. for 26.5 hours, after which they were transferred to a single-necked flask for reduced-pressure, short-path distillation. The monoadducts were distilled away from the diadducts. The pure diadducts were recovered in 81% yield, based on charged mass, and had a saponification number of 678 and a dropping point of 112.4° C.

EXAMPLE 3

A 250 ml flask was charged with 147 g (1.5 mol) maleic anhydride and heated to 190° C. under an inert atmosphere. During the course of 4 hours, 102 grams (0.74 mol) of 98% pure delta-3-carene were added to the molten maleic anhydride. The reactants were thereafter maintained at 190° C. for 25.5 hours, after which they were transferred to a single-necked flask for reduced-pressure, short-path distillation. The monoadducts were distilled away from the diadducts. The pure diadducts were recovered in 73% yield, based on charged mass, and had a saponification number of 671 and a dropping point of 125.6° C.

What is claimed is:

1. A composition of matter comprising the diadduct product of delta-3-carene and a Diels-Alder dienophile.

2. The composition of claim 1 wherein the dienophile is maleic anhydride.

3. A delta-3-carene adduct composition comprising a delta-3-carene diadduct being substantially free of a delta-3-carene monoadduct.

4. The composition of claim 3 wherein the composition comprises about 30% by weight or less of the monoadduct.

5. A process for the preparation of a carene diadduct in high yield which comprises
    (a) providing a mixture of a Diels-Alder dienophile and delta-3-carene in a molar ratio of at least 1.5:1; and
    (b) reacting the dienophile and delta-3-carene at a temperature of at least 150° C. to provide a reaction product that is greater than about 50% by weight diadduct.

6. The reaction product prepared by the process of claim 5.

7. The process of claim 5, wherein said dienophile is selected from the group consisting of maleic anhydride, itaconic anhydride, a maleimide, a fumarate, acrylonitrile, acrylic acid, a lower alkyl ester of acrylic acid, methacrylic acid, a lower alkyl ester of methacrylic acid, and mixtures of these.

8. The process of claim 5 wherein said dienophile is maleic anhydride.

9. The process of claim 5 comprising the further step of separating the diadduct from any monoadduct.

10. The process of claim 9 wherein said separating step comprises distillation.

11. The process of claim 8 wherein said mixture is formed by heating delta-3-carene to a temperature of at least 150° C. and then adding the maleic anhydride to the delta-3-carene.

12. The process of claim 8 wherein said mixture is formed by heating the maleic anhydride to a temperature of at least 150° C. and then adding the delta-3-carene to the maleic anhydride.

13. The process of claim 12 wherein the maleic anhydride is heated to a temperature of at least about 165° C. prior to addition of the carene, the reaction temperature is at least about 165° C., and the reaction is conducted in the absence of solvent.

14. The process of claim 8 wherein the molar ratio of maleic anhydride to delta-3-carene is about 2-3:1.

15. The process of claim 13 wherein the molar ratio of maleic anhydride to delta-3-carene is 2-3:1.

16. The process of claim 8 wherein said reaction is conducted in a solvent that is capable of inhibiting the formation of free radicals.

17. A process for preparing an epoxy resin characterized by having a high glass transition temperature comprising
    (a) providing a diadduct obtained by reacting a mixture of maleic anhydride and delta-3-carene in a molar ratio of at least 1.5:1 at a temperature of at least 150° C.; and
    (b) reacting said diadduct with an epoxide compound.

18. The process of claim 17 wherein the reaction of step (a) is conducted at a temperature of at least about 165° C.

19. The process of claim 17 wherein the epoxide compound is the condensation product of epichlorohydrin and a bisphenol.

* * * * *